(12) United States Patent
Peltz (10) Patent No.: US 6,205,716 B1
(45) Date of Patent: Mar. 27, 2001

(54) MODULAR VIDEO CONFERENCE ENCLOSURE

(76) Inventor: Diane P. Peltz, 203 Trafford La., Savannah, GA (US) 31410

( * ) Notice: Subject to any disclaimer, the term of this patent is extended or adjusted under 35 U.S.C. 154(b) by 0 days.

(21) Appl. No.: 09/478,852

(22) Filed: Jan. 7, 2000

Related U.S. Application Data (63) Continuation-in-part of application No. 08/753,478, filed on Nov. 26, 1996, now abandoned
(60) Provisional application No. 60/007,927, filed on Dec. 4, 1995.

(51) Int. Cl.[7] .............................. E04H 1/14; A47B 81/06; H04M 11/00; H04N 7/15
(52) U.S. Cl. ............................. 52/36.2; 52/27.5; 52/79.1; 345/330; 345/905; 348/15; 348/383; 379/453
(58) Field of Search ..................................... 52/36.1, 36.2, 52/79.1, 27.5; 345/330, 905; 348/15, 383; 379/453

(56) References Cited

U.S. PATENT DOCUMENTS

| | | |
|---|---|---|
| D. 294,204 | 2/1988 | Tombs et al. . |
| D. 302,907 | 8/1989 | Otto et al. . |
| D. 338,513 | 8/1993 | O'Neill . |
| D. 339,251 | 9/1993 | Gainey, Jr. . |
| D. 355,989 | 3/1995 | Raynor . |
| 3,498,011 * | 3/1970 | Lindgren . |
| 3,553,911 | 1/1971 | Morrow et al. . |
| 3,845,590 * | 11/1974 | Ertl ........................................ 52/36.1 |
| 3,959,607 * | 5/1976 | Vargo ...................................... 379/453 |
| 4,173,024 * | 10/1979 | Miller ..................................... 358/115 |
| 4,505,078 | 3/1985 | Huh . |
| 4,594,817 | 6/1986 | McLaren et al. . |
| 4,667,580 | 5/1987 | Wetzel . |
| 4,758,887 | 7/1988 | Engel et al. . |
| 4,845,636 * | 7/1989 | Walker ............................ 364/479.07 |
| 4,902,881 * | 2/1990 | Janku ..................................... 235/381 |
| 4,960,117 | 10/1990 | Moncrief et al. . |
| 5,177,912 | 1/1993 | Ball . |
| 5,289,287 | 2/1994 | Dargis et al. . |
| 5,382,972 * | 1/1995 | Kannes ...................................... 348/15 |
| 5,393,964 * | 2/1995 | Hamilton et al. ..................... 235/381 |
| 5,572,005 * | 11/1996 | Hamilton et al. ..................... 235/381 |
| 5,604,341 * | 2/1997 | Grossi et al. ......................... 235/379 |
| 5,615,623 * | 4/1997 | Capraro ............................. 52/36.1 X |
| 5,638,646 | 6/1997 | Shane . |
| 5,653,063 * | 8/1997 | Barnett et al. ............................. 52/29 |
| 5,727,353 * | 3/1998 | Getz et al. ............................. 52/79.1 |
| 5,897,325 * | 4/1999 | Koby-Olsen .......................... 434/432 |
| 5,993,216 * | 11/1999 | Stogner .................................. 434/29 |
| 6,046,761 * | 4/2000 | Echerer ................................... 348/13 |

* cited by examiner

*Primary Examiner*—Robert Canfield
(74) *Attorney, Agent, or Firm*—Clyde N Christofferson (57) ABSTRACT

A secure, modular and movable interactive two-way telecollaborative video conferencing and imaging enclosure for conducting business or privileged medical, legal, or other confidential matters in private, being particularly equipped for remote monitoring of physiological attributes of one or more users by medical specialists and remote interaction between users and medical specialists.

9 Claims, 7 Drawing Sheets

MODULAR VIDEO CONFERENCE ENCLOSURE

This application is a continuation-in-part of application Ser. No. 08/753,478 filed on Nov. 26, 1996, now abandoned, said pending application claiming the benefit of Provisional Application Ser. No. 60/007,927 filed on Dec. 4, 1995.

BACKGROUND OF THE INVENTION

1. Field of the Invention

The present invention generally relates to remote telecollaborative conferencing and in particular to modular and secure enclosures equipped therefore.

2. Background Description

This invention relates to the fields of booths, kiosks, or shelters, and conducting two-way interactive videoconferencing from inside enclosed shelters. While open communication kiosk solutions are in wide-use for public informational use, most, if not all of these kiosks are of an open design, with at least one wall missing allowing for limited privacy for users conducting personal or confidential business matters.

Today two-way video conferencing is commercially readily available. Yet, the public at large has little accessibility to a video conferencing system. When public accessibility is available, it is generally from an open kiosk with little or no privacy from the people standing near you while you transact your business. If kiosks offer video conferencing opportunities, most of these open informational kiosks have only one-way reception of video from a remote site toward the user in the open kiosk. This is limiting as the user can be heard, but generally not seen on the remote end.

Most often, users of two-way video conferencing are limited to conducting point-to-point meetings, or multipoint meetings, from a desktop computer, or from a roll-about room unit, or from an open three sided kiosks, or from a dedicated boardroom or conferencing room. Video conferencing rooms, while closed and allowing for privacy, are not transportable. Once a video conferencing system is in a room and wired, if the users move, the infrastructure to the video conferencing integration stays behind, as does sometimes the built-in room cabinetry.

SUMMARY OF THE INVENTION

It is therefore an object of the present invention to provide a fully enclosed, secure, moveable, interactive two-way video conferencing shelter which will open up a new channel of distribution for two-way video conferencing.

A further object of the invention is to provide a secure, modular and movable interactive two-way telecollaborative video conferencing and imaging enclosure for conducting business or privileged medical, legal, or other confidential matters in private, being particularly equipped for remote monitoring of physiological attributes of one or more users by medical specialists and remote interaction between users and medical specialists.

The basic purpose of this invention is to provide an enclosed, transportable, secure interactive two-way telecollaborative video conferencing and imaging enclosure for people to sit in or lay in, and conduct their business or privileged medical, legal, or other confidential personal matters in private.

This invention provides an interactive electronic means to bring healthcare professionals to the patients, a means to train and educate students of the healing arts at a distance, and allows the collection of statistical data through the use of video conferencing equipment, cameras, sound, light, and other measurement and data warehousing equipment and devices.

The preferred embodiment of this invention is equipped with electronic equipment, such as a video conferencing system, a computer monitor and computer processing unit, a video cassette recorder (VCR), a control pad that is advantageously located on the user console and preferably embedded in the console. This control panel is situated for easy access and readability by the user, and allows for push-button access to various features enabling the user to seamlessly connect to other video conferencing units. A telephone set may be hung on the firewall in some embodiments, or placed next to the touchpad on the console.

Various other possible equipment is used in these units depending on the applications, or business, conducted from these shelter units. While other embodiments for the invention are possible, it is the two-way video conferencing applications with specific uses, such as telemedicine and distance learning that will required application-specific peripherals to be added. This invention will provide the electronic means and the medical peripherals, and anatomy measuring devices to measure sound, light, and electrical movement of the energy of the human body, as well as the energy fields surrounding the human body to assess the over-all health of the population using these assessment and diagnostic enclosures. The generic embodiments will have locked equipment cabinets, and a security entrance system, such as a magnetic cardreader to insure greater security access. All embodiments of the enclosed, two-way interactive video conferencing shelters will have appropriate equipment and lighting to conduct effective video conferencing meetings. The preferred embodiment of the smaller enclosed booth/kiosk shelters are portable and modular in design; to set up, break down and easily move with rest of furniture. A larger enclosed video conferencing shelter preferred embodiment is movable on tractor-trailer wheels, or on a flatbed and moved on railroad tracks, or even in the hole of a ship. These shelters, once they reach their destination, can be placed on the ground as a temporary permanent structure and then moved again as needed. All embodiments of this invention are wheelchair accessible.

Determining what applications are to be conducted over the video conferencing system will include selecting and installing in the various embodiments of this invention specialized equipment ranging from graphics and document cameras, video cassette recorder, slide projectors, fax machines, personal computers, and a host of software to conduct electronic billing, scheduling software, imaging and administrative document imaging and record keeping, and carriers necessary for delivering voice transcription and to effectively conduct a two-way video conferencing session or meeting.

In the preferred embodiment of the invention, all sides of the invention are connected together providing an enclosed shelter for the users of video conferencing. The shelter has a door, a roof, and a floor. The user, upon shutting the door behind upon entry into the two-way video conferencing booth/kiosk shelter, sits in front of the video camera and monitor, picks up the telephone unit and conducts a two-way videoconference call. The electronic equipment of this invention is placed behind a firewall in the one-person enclosures. In the larger enclosures, the equipment is stacked securely behind various structures. All the equipment, due to the enclosed features of this invention, is locked behind doors; this deters theft of the electronics.

Theft and vandalism deterrence is also accomplished by the use of a smart card or creditcard swipe at the entrance of the preferred embodiment; the use of such a smart card or creditcard provides an electronic record of any users, enables easy access to billing, and acts as a further deterrent to vandalism and theft.

A possible alternative to the embodiment of the invention is to enhance the security level of shelter and install metal sensors attached to the frame or outside the frame for high security areas (such as prisons) in order to prevent pens (or sharp instruments) leaving the shelter. The shelters can embody electronic security embedded in the frame or in outside materials of the shelters; and, can be equipped as a shielded shelter.

To measure electromagnetic fields, or the energetic system of the body with noninvasive technical instruments, this invention houses medical peripherals, sensors, or devices such as, but not limited to a generator of a complex energy wave, having audio, radio and light components, including an audio frequency oscillator, a radio frequency transmitter, a radio frequency amplifier, an antenna tuner, an antenna, tuned coaxial cables and an optional reverberation unit.

These and other peripherals allow clinicians "to see" or "perceive" sound. This invention utilizes sonification (defined as the use of nonspeech audio to convey information. More specifically, sonification is the transformation of data relations into perceived relations in an acoustic signal for the purposes of facilitating communication or interpretation.) Sonification conveys information to a human listener by mapping data onto perceived relations in an acoustic signal, such as the Pulse-oximeter medical peripheral of this invention that produces a tone that varies in pitch with the level of oxygen in a patient's blood, allowing the doctor or clinician to monitor this critically important information. In a more specialized scientific domain an effective means of presenting infrared spectrometry data via several complementary mapping schemes is one example of "diagnostic" sonification specifically designed for a special needs population, such as blind patients.

Schemes for auditory rendering of maps and diagrams embedded in text and scanning arbitrary visual images and presenting them in sound are currently being developed and will play an important part in the assessment of human health in this invention in the future with equipment, peripherals, software applications and devices that will include novel ways of using sound sensors to explore complex data sets, to supplement other sensory modalities for data communication, and to assist special user populations.

Other peripherals will be cameras that photograph the energy flow (or aura photography such as demonstrated with the Kirlian Camera). These devices will allow the process that measures the Electro Magnetic Field around the body.

This invention includes such other peripherals or devices as a therapeutic use of magnetic field therapy and far-infrared technology û devices both complementary medicine and alternative healthcare can use to assess health, reduce stress, promote healing, and speed recovery.

The human brain waves are in tune with geomagnetic waves, which have a basic frequency range between 1 and 24 Hertz, with peaks in the megahertz region. Medical devices that assist the autonomic nervous system to overcome environmental stress symptoms will be a part of the healing application. By applying pulsations through a transmitter by various Hertz frequencies to patients through various settings to balance natural and magnetic fields.

This invention houses a peripheral that uses light in the measurement and treatment of pain, such as an electronic light therapy device which uses low energy infrared light with a wavelength of 660 nano-meter to activate enzymes around nerve endings to reduce pain and promote a natural healing process. Another peripheral that uses a large gas tube (an x-ray bulb shaped tube, filled with a mixture of Helium and Neon gas ionized by RF frequencies at a power of 50 watts) has proven effective in the treatment of vibrational or energetic treatments.

This invention provides two-way interactive video conferencing, and has a preferred embodiment of the enclosed units being transportable. For instance, the preferred embodiment of the shelters are modular, with the design easily broken down into transportable pieces fitting through regulation size house doors for moving and assembling. The transportability of the smaller shelters allows for the shelters to be moved to other locations and not be left stationary as part of a room, such as in a video conferencing room The larger embodiments of the invention are transportable and can be placed on flat bed units, moved over the road via tractor-trailer or built as a railroad car shelter.

Another possible embodiment for this invention is to configure the shelters to operate as a complete business office, educational training office, legal office, telemedicine operating room, or as a classroom or video conferencing room with several stations. The various equipment and peripherals are subject to the needs of the applications or uses. All installations for the operation of the diverse equipment in the preferred embodiment of the shelters are stored in the chimney of the shelter. This has the advantage that exposed cable does not exist, and fire codes are met.

Figure 10:
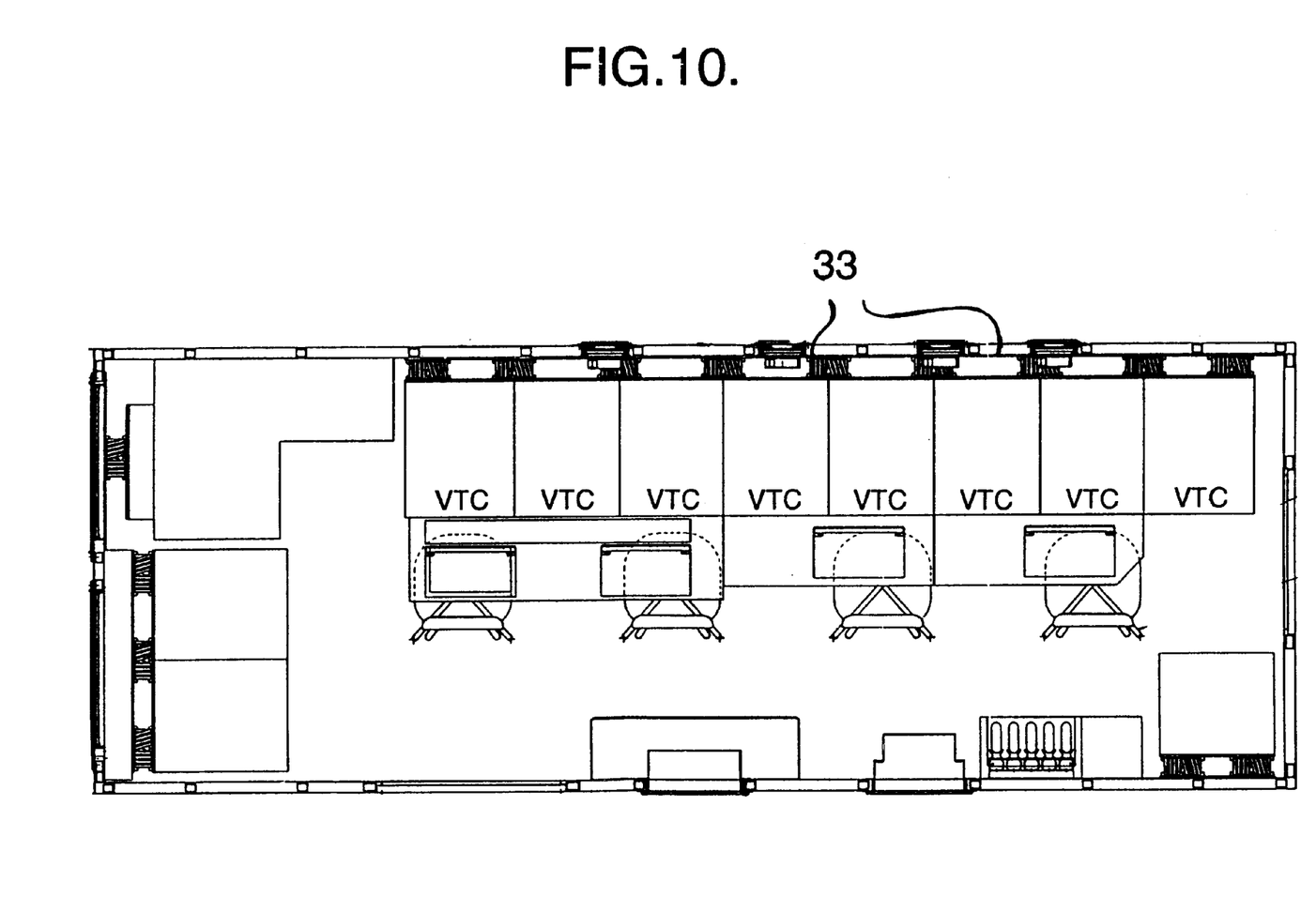
FIG. 10 shows a view of one floor plan for multiple stations on larger embodiments of the invention.
Figure 11:
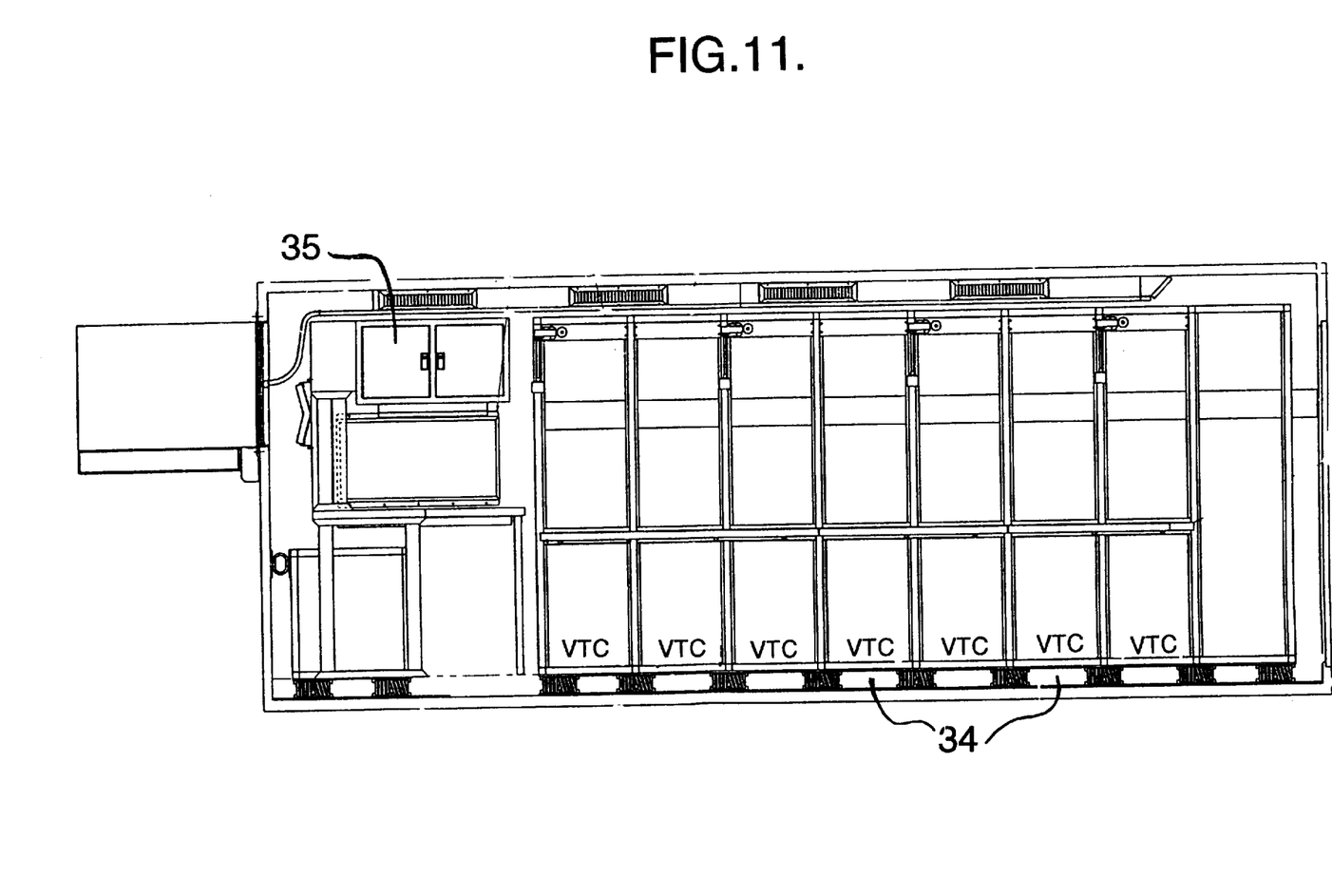
FIG. 11 shows a curbside view of Prototype Three with video conferencing equipment view, storage, and electrical supply and connections box.
Figure 12:
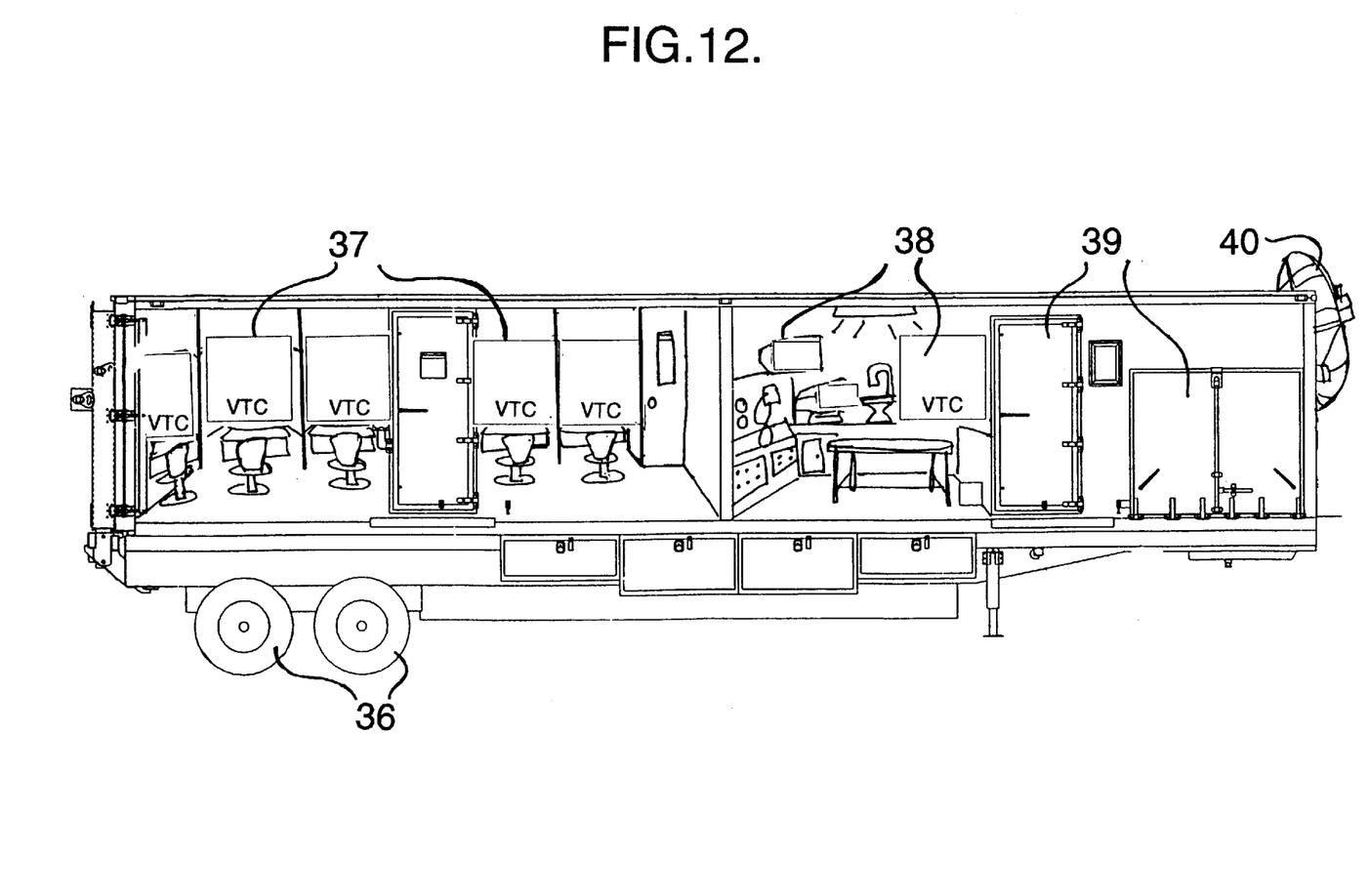
FIG. 12 is an exterior curbside view of a preferred embodiment of the invention for a training and teaching hospital application.

Since the filing of the provisional application, the inventor has built two actual prototypes illustrating the preferred embodiments of this invention. The prototypes of this invention have been beta-tested for video and audio capabilities as specified in the detailed section of these specification, and as shown in the drawings FIGS. 1 through 9. The preferred larger, transportable embodiments of this invention are illustrated in the drawings as shown in FIGS. 10 through 12 that focus on telemedicine training centers. Each embodiment of the invention connects fully to other video conferencing units and locations whether in point-to-point connections, or multipoint conferencing via selected terrestrial or satellite transmission carriers.

This invention can provide a telemedicine healthcare service that is open to the public The patients would access this invention with a smart card (Charge cards such as MasterCard, VISA, or an insurance card, or HMO card, or other cards set up to enter the invention). These smart cards upon entering the invention would identify users as existing patients of an HMO, or independent insurance coverage, or as an independent user without insurance in need of a health assessment or diagnostic visit.

Smart cards protect the privacy of records, provides information in emergencies, and can be a help for physicians, clinicians, and patients to track services and medications. Upon entering the unit(s) representatives would conduct an initial screening, or health assessment interactively over video conferencing, audio conferencing, or by computer. If required, the representatives would connect the patient up with their HMO to an installed telemedicine center at the HMO, private alternative healthcare clinic/facility, or hospital that was set up to conduct a telemedicine consultation.

If a visit with a preferred physician or clinician was not required, and the representatives will address the patient needs (by addressing an on-call doctor per arrangements with various HMOs, etc.), conduct a healthcare assessment or diagnostic screening, and the patient would be given immediate feedback, or sent on their way with instructions to contact their healthcare provider. TM A business model is a VIKI™ unit is set up in a drug store. Patient One goes to the drug store and uses the VIKI™ for follow-up care. The HMO representative answers the call from inside the unit, and the Patient One has a consultation. Patient One actually belongs to a HMO. If Patient One upon initial assessment needs no further referrals, it is charged to the HMO electronically. Or, if Patient One needs further attention, or a referral, then Patient One is referred to a Kaiser HMO telemedicine center (actually the videoconference is rolled-over to them electronically by the representative). Patient One can then speak directly with a physician from their HMO via video conferencing or a representative alternative healthcare professional subcontracted by their HMO).

Or, Patient One can be referred to an actual office/HMO clinic and the representative generates an appointment automatically with the HMO, or reservation software inside the invention before they leave said invention. If the visit reveals the patient has a health emergency, or needs immediate medical attention, Patient One is instructed to go directly to the HMO clinic or the local health providing institution.

Patient Two is next, puts in their smart card and connects with a medical representative. Again a health assessment is conducted. Patient Two needs to discuss compliance on a drug or homeopathic prescription and if the prescription is already written. The connecting representative will provide all the necessary connections, as no referral is necessary. Patient Two goes home.

An Electronic Data Service (EDS) is connected to the entry identification method (i.e. smart card, fingerprint, voice or retina recognition) to handle all information instantly with programs written for certain symptoms and pathways to symptoms. The medical or alternative clinician representatives have access to these pathways. This EDS is set up to route the user profiles into the tracking and billing system matching them with their insurance providers. Indigent populations will have special funding set up, and connections (on the system) to physicians or healthcare clinicians that would accept them.

This invention provides medical assessments and diagnostics to a broad sector of public traffic walking through the drug stores, or malls, or other widely trafficked access points will bring medial services to the people, rather than the people to the medical services. Some Alternative Medical practices well-suited for this invention are, but not limited to: Chiropractic and EAV (Electro-Acupuncture According to Dr. Voll), Color Therapy, Music/Sound Therapy, Detoxification: Fasting Therapies, Herbal Medicine, Vitamins and Supplements, Weight Management, Dream Work, Kinesiology, Homeopathy and Naturopathic Medicine, Bioenergetics, Biofeedback, Biorhythms, Cognitive Therapy, Light Therapy, Meditation, Acupuncture and Acupressure, Ayurvedia and Tibetan Medicine, and Chinese and Japanese Medicine.

This enclosed booth/kiosk with conferencing connections to participants at different locations is well-suited for security-conscious conferences of a private nature including, but not limited to such applications as legal and health matters conducted from secure facilities such as prisons, to public health and diagnostic matters, criminal justice matters, public and private education and vocational training, and national and international security applications.

The invention is an enclosed, secure, transportable shelter that features interactive, two-way video conferencing equipment. People actually sit inside, and close a wheelchair accessible door to conduct business or have a personal, private two-way video conferencing conversation. The invention offers a variety of embodiments ranging from a smart card or credit card accessible shelter to be placed in high-trafficked public areas, to large over the road shelters on wheels. These shelters are modular, meaning they can be broken into moveable pieces for easy transporting. Alternative embodiments of this invention are shelters that are equipped for a specific application or group use, such as for medical or healthcare use. In these alternative two-way interactive telemedicine video conferencing shelters, patients have the electronic video presence of a physician or clinician at remote sites to help guide them through a health assessment, examination, X-rays, diagnostics, surgery, and attending paperwork.

The invention relates to an enclosed modular, and moveable, booth/kiosk designed to house one or more participants to enable participants to conduct private business and diagnostics with the use of two-way interactive video conferencing and imaging hardware and software tools. Each enclosed booth/kiosk is tailored to the requirements of a client's applications in regard to software, hardware, telecommunications carriers and connections, point-to-point or multiple locations, and other criteria.

Enclosed booth/kiosks are used in matters of high security meetings, legal counseling, medical and health diagnostics and counseling, and other applications needing security measures and privacy.

A video conferencing enclosure having a highly developed security system and usable for business matters, and matters of private and personal natures, such as, but not limited to matters concerning: legal counseling, top security matters, environmental matters, global economics, training and education, financial services, and medical matters concerning physical health, mental health, emotional health, and spiritual health.

The booth's software and hardware will be video conferencing and preferred for communication purposes since the remote participants can see one another, and so that mimic and gesture can come into play, or for diagnostic matters, so that physicians or clinicians can view the participants physical body and mannerisms to detect illness, or physiological and emotional gestures and nuances.

With the visual presence of a participant added to multimedia tools and graphics, document imaging, and telecollaborative software, this full electronic face-to-face approach of a modular security sensitive kiosk/booth that houses one to three people (or more) is a preferred choice rather than conducting business and matters of a private nature in an open area without walls.

While the video conferencing monitor will be a touch sensitive monitor, the work place in front of the video conferencing equipment will be large enough to hold an graphics electronic pad and pen to permit signatures and telecollaboration work. Telecollaboration, or work share allows various participants from several locations to interact on documents by drawing lines and edits on screen. All other electronic hardware and software are positioned behind a cutout frame. This has the advantage that exposed cable does not exist and tampering with cables and security measures are avoided. In order to provide this booth/kiosk to external locations to be placed in temperature extremes, the insulation and weatherproofing of the booth/kiosk is constructed to accommodate the extremes of weather. Appropriate transmission and telecommunications carriers are designated to connect remote participants to services or business desired.

The booth/kiosk is built with a smart card or electronic card entrance. This feature allows for clearer security use, and record keeping of use, or with fingerprint recognition for entrance, or with voice recognition, or with pattern-recognition software for security purposes.

Each kiosk/booth is vented air-conditioned, or heated dependent on the external conditions and client specifications. The remote location can be another booth/kiosk, or a desktop video conferencing unit, or a video conferencing room, or a roll-about unit, or any type of video conferencing equipment, connected by analogue or digital signals, that will interoperate with the invention.

The video conferencing booth/kiosk will house a wide range of diagnostic imaging equipment for medical applications. Participants can converse with and see technicians or clinicians at remote sites. The booth/kiosk can serve as an educational personal classroom, or counseling booth, to provide health care services to remote patients. It is used within a large medical complex to increase patient load, speed prognoses and improve consultations.

The booth/kiosk has at least one picture-screen apparatus arranged in the inner panel of the kiosk at eye level, and in range of view of the conference participant, whose work area is directly in front of the participant. The work area will have an electronic writing tablet and pen, to electronically sign legal and binding contracts and documents appearing on the picture screen.

The enclosed booth/kiosk is designed to be wheel chair accessible, from the back of the one-person enclosed booth/kiosk, or from the side of the three-person model. Models are designed to house more equipment, such as, but not limited to: Terminal adapters for the high-speed, digital ISDN telephone service and a combination of hardware and software that allows users to access all services at super speeds; the ability to download digital or analog video clips, X-rays, charts, music, speeches, high-resolution color photographs, send and receive massive data files fast; desktop publishing documents, spreadsheets, engineering data, telemedicine, teleradiology, and diagnostic scanning information.

All configurations and installations for the operation of the video conferencing kiosk/booth are stored in the kiosk/booth. This has the advantage that exposed cable will not exist and "cable bundles" are avoided. During multipoint meetings, a split screen is available to view all interactive or non-interactive participants.

The invention provides a modular, moveable, security sensitive, enclosed video conferencing booth/kiosk to house a person, or persons, to conduct private and privileged consultation or discussions over two-way interactive video conferencing from a variety of places, including, but not limited to spaces that is a permanent part of an existing building, or from a facility that is but a remote, outdoor rugged terrain with changing and inclement weather. There are replaceable panels in the design that are replaceable if damaged, similar to replaceable parts on an automobile, such as a fender.

The booth/kiosk is accessible on the one-person model from the rear, and the three-person model from the side. This same booth seat is a medical bench in medical-use applications. It is positioned flush against the interior posterior wall to provide wheel chair accessibility. The participant can lie down for diagnostic scanning or robotics probing examinations.

The internal video conferencing equipment includes, but is not limited to, video conferencing hardware and software, electronic scanner(s), sound equipment and microphones, an interactive graphics electronic pad, a printer, and other application specific appropriate hardware and software. By putting more participants on-screen, the video conferencing feature is said to make video conferencing more realistic, showing listener reactions that might go unseen without video component. For instance, with a panel reviewing a parole candidate in a prison system; or social workers, psychiatrists, scientists and clinicians reviewing a case; or educators conducting training; or participants conducting security negotiations this feature is invaluable.

The moveable shelters can travel to various locations and function for example, as teaching hospitals, or on-the road welfare-to-work training laboratories. The two-way interactive video conferencing shelters are transportable over land, sea and air. Application specific equipment can be installed in this invention, regardless of size, to better serve the fields of medicine, law, finance and business, distance education and training, social services, top-security sectors, and other fields. This invention addresses a need for an enclosed, private alternative to open video conferencing kiosks, open desktop areas, and stationary, fixed, unmovable video conferencing rooms.

BRIEF DESCRIPTION OF THE DRAWINGS

The foregoing and other objects, aspects and advantages will be better understood from the following detailed description of preferred embodiments of the invention with reference to the drawings, in which.

DETAILED DESCRIPTION OF A PREFERRED EMBODIMENT OF THE INVENTION

Figure 1:
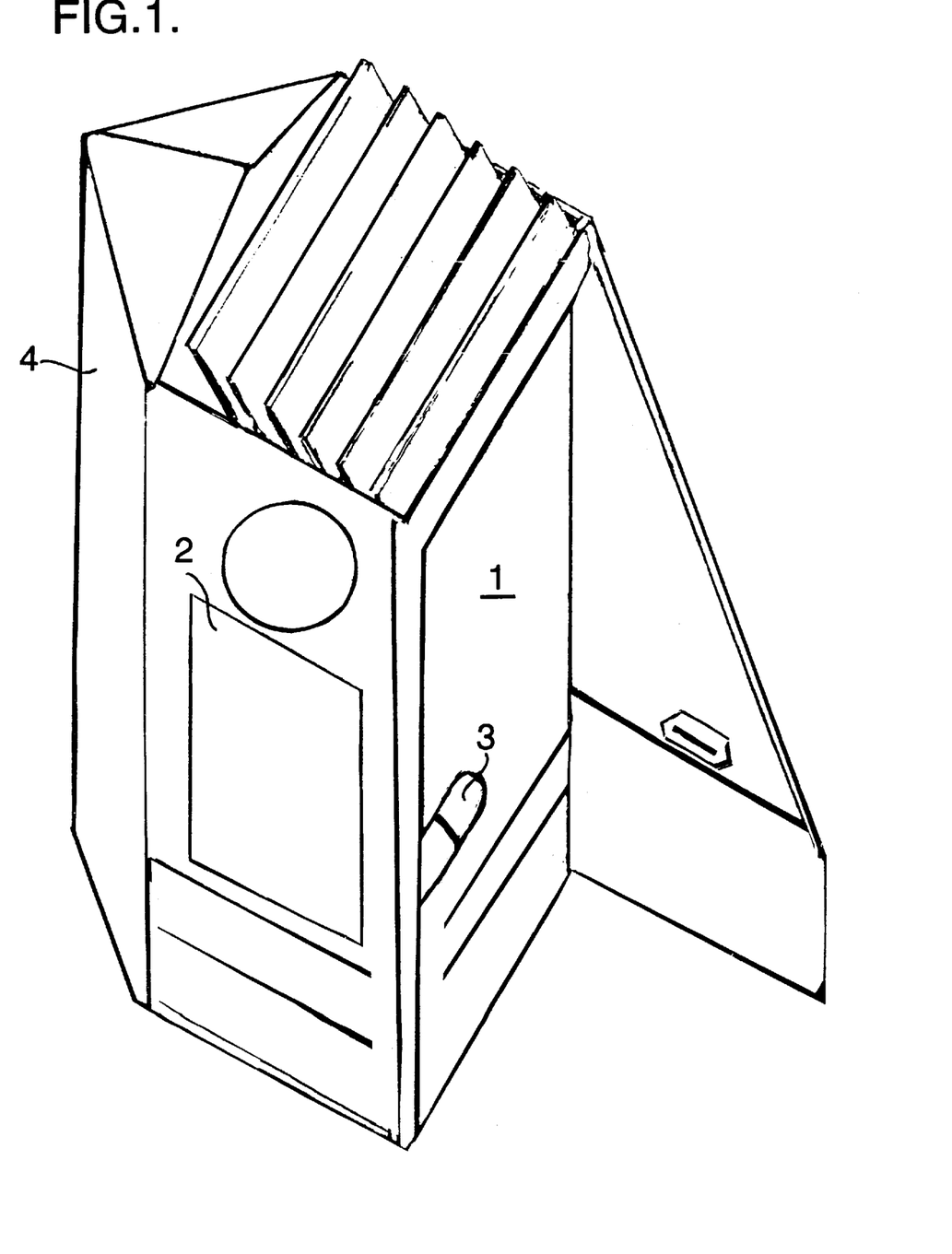
FIG. 1 is an artist perspective rendering of an implementation of the invention designed for one-person.
Figure 2:
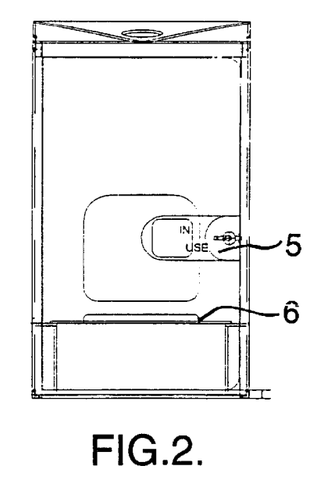
FIG. 2 is a front view of a one person implementation showing in-use sign and seat.
Figure 3:
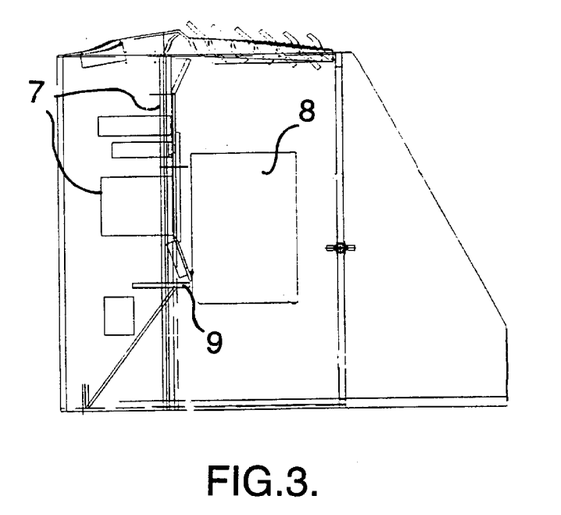
FIG. 3 is a view of the invention showing a back wall and window with an equipment stacking rack.
Figure 4:
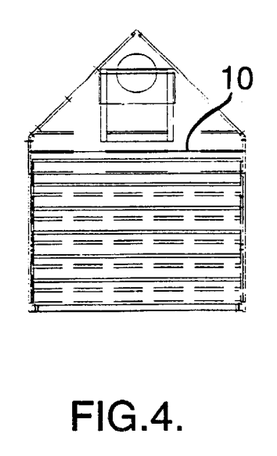
FIG. 4 is a top view of the invention.
Figure 5:
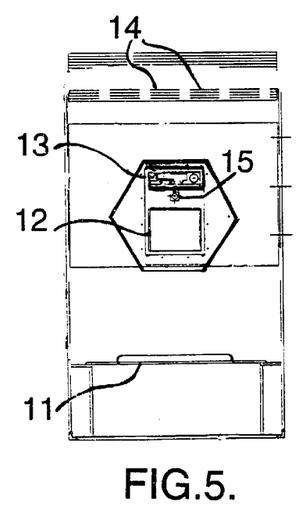
FIG. 5 is a view from inside the enclosure of the invention.
Figure 6:
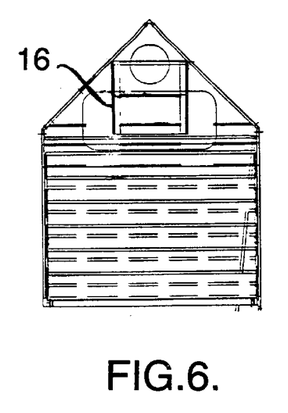
FIG. 6 is a top view of the invention.

Referring now to the drawings, and more particularly to FIGS. 1 through 12, there is shown implementation of the invention in three prototypes. FIGS. 1 through 6 show Prototype One. FIG. 1 is an artist perspective rendering of an embodiment designed for one-person. It shows a wheelchair accessible door (1), windows (2), smart card or credit card access (3), and in-use sign and locked equipment storage cabinet (4). FIG. 2 is a front view showing in-use sign (5) and seat (6). FIG. 3 is a back wall and window view showing equipment stacking rack (7); rectangular window design (8); touch screen and telephone console (9) attached to front of firewall. FIG. 4 is a top view showing a vented top roof (10) design. FIG. 5 is a view from inside the enclosure showing conferencing on a monitor; the seat position (11); a video conferencing monitor (12); a Video Cassette Recorder (VCR)(13); some vents in roof (14), and a camera mount (15). FIG. 6 is a top view with a rack and stack unit (16) in the equipment cabinet section of the enclosure.

Figure 7:
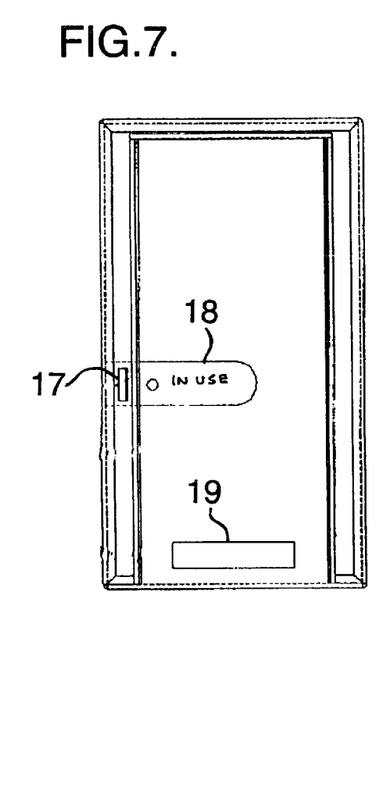
FIG. 7 is a front view of Prototype Two embodiment.
Figure 8:
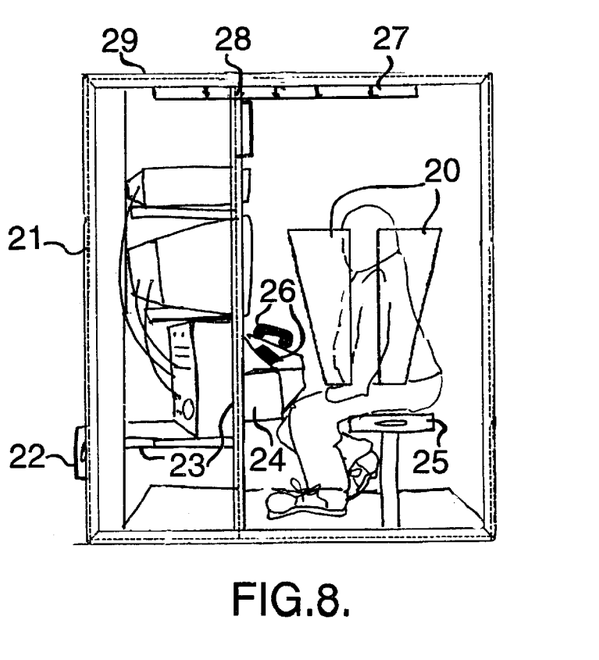
FIG. 8 is a side view of the Prototype Two implementation of the invention.
Figure 9:
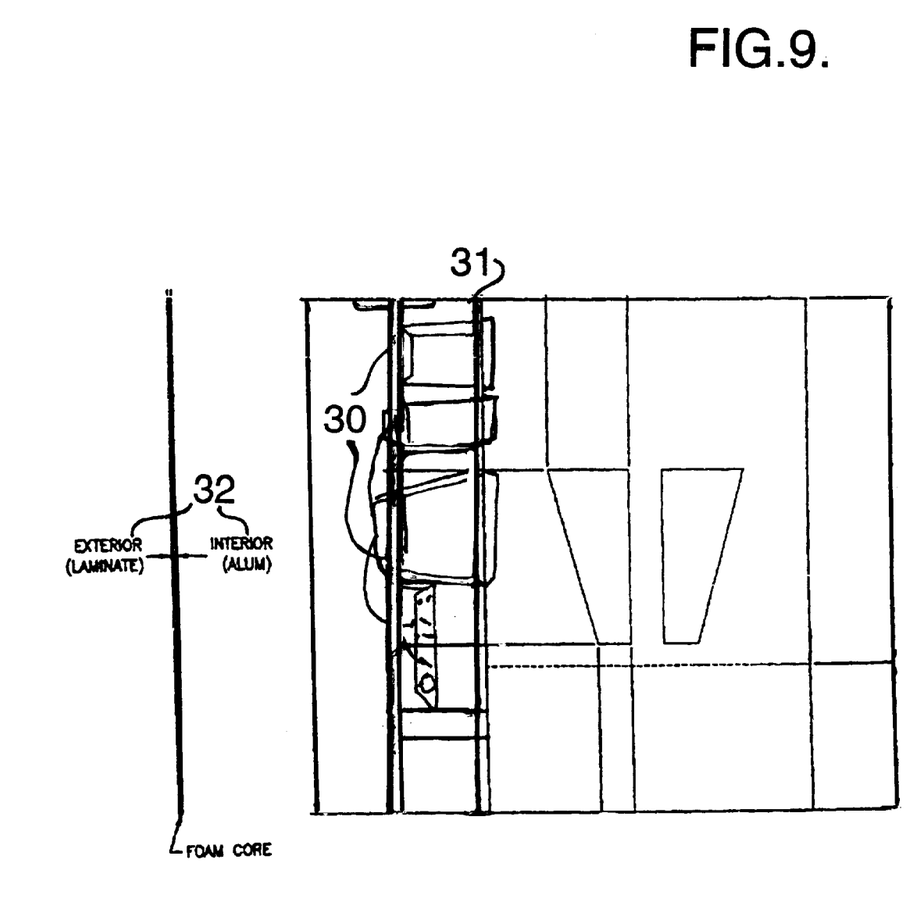
FIG. 9 is a side view layout of the enclosure highlighting placement of rack and stack of video conferencing equipment and also indicating materials structure used for the enclosure.

FIGS. 7 through 9 show a second embodiment of the invention, Prototype Two. FIG. 7 is a front view of the invention showing a smart card or credit card entrance and swipe slot (17), an in use lighted sign (18) and front vents for air flow (19). FIG. 8 is a side view of the invention showing V shaped windows (20) in see-through glass, one-way mirrors, smoked or other types of glass; a back door (21) to enter equipment cabinet with a lock on the door; a plug in (22) for communications interface with RS232 modem connections; a rack and stack (23) of electronic equipment including, but not limited to, equipment such as VCR, video conferencing equipment, Central Processing Units (CPU), computer monitor, codecs, audio equipment and speakers; a user console (24) that interfaces with the equipment and has a pull out writing shelf; a user seat (25); a telephone and electronic touch pad (26) on the user console for easy accessibility from the seat; lights (27) to illuminate user for video camera shoot; a firewall (28) between the user and the equipment cabinet portion; and airvents (29) in the ceiling. FIG. 9 is a layout showing the placement of rack and stack of video conferencing equipment (30) and firewall (31). Also shown in FIG. 9 is an example of materials used in the walls (32) of the enclosure: foam core is installed between laminate and aluminum for greater density and improvement of audio and sound.

FIGS. 10 through 12 show a third design for larger embodiments of the invention, Prototype Three. FIG. 10 shows a view of one floor plan (33) for multiple video conferencing stations (VTCs). FIG. 11 shows a curbside view of Prototype Three with video conferencing equipment view (34), storage, and electrical supply and connections box (35). FIG. 12 is an exterior curbside view of a preferred embodiment of the invention for a training and teaching hospital application. There is shown a flatbed design of a shelter on wheels for easy transporting (36); computer and video conferencing training section of a shelter (37); telemedicine (medicine conducted through video conferencing over a distance via communications links such as satellite or terrestrial transmission) including a Hospital and Medical Training section with video conferencing equipment, operating table, illustrated sterile medical storage, and medical peripherals (38); and medical entrance doors, with the shorter doors equipped with a platform and hydraulic lift (not shown) for better access to patients in wheelchairs or on stretchers and gurneys (39); and a satellite dish connected to rear of trailer to receive and transmit two-way video conferencing signals (40).

FIGS. 1 through 12 may be further understood by reference to the following list of items identified by reference numerals on the figures:

For FIG. 1—One-person booth/kiosk shelter artist rendering of design for Prototype One of the invention, the following reference numerals:

1. Wheelchair accessible door
2. Windows-smoked or clear or two-way mirror
3. Smartcard or creditcard access and in-use sign
4. Locked equipment storage cabinet For FIG. 2—Front view/look of Prototype One of the invention, the following reference numerals:

5. In-use sign
6. Seat position shown

For FIG. 3—Back wall and window-view of Prototype One of the invention, the following reference numerals:

7. Equipment stacking rack shown
8. Window rectangular design shown
9. Touch screen and telephone console attached to front of firewall For FIG. 4—Top view of Prototype One of the invention, the following reference numerals:

10. Vented top roof design on prototype one

For FIG. 5—Sitting inside the enclosed booth/kiosk shelter looking at video conferencing on monitor in Prototype One drawing, the following reference numerals:

11. Seat
12. Video conferencing monitor
13. Video Cassette Recorder (VCR)
14. Vents in roof
15. Video conferencing camera For FIG. 6—Top view of Prototype One drawing of the invention, the following reference numerals:

16. Rack and stack unit in equipment cabinet section of booth/kiosk shelter

For FIG. 7—Front view Prototype Two embodiment design of the invention, the following reference numerals:

17. Smartcard or creditcard entrance and swipe slot
18. In-use lighted sign
19. Front vents for airflow For FIG. 8—Side view of Prototype Two of the invention, the following reference numerals:

20. V shaped windows in see-through glass, one-way mirrors, smoked or other types of glass
21. Back door to enter equipment cabinet with lock on door
22. Plug in for communications interface with RS232 modem connections
23. Rack and stack of electronic equipment including, but not limited to equipment such as VCR, video conferencing equipment, Central Processing Units (CPU), computer monitor, codecs, audio equipment and speakers
24. User console that interfaces with equipment, and pullout writing shelf
25. User seat
26. Telephone and electronic touchpad on user console for easy accessibility from seat.
27. Lights to illuminate user for video camera shoot
28. Firewall between user and the equipment cabinet portion
29. Airvents in the ceiling of Prototype Two design For FIG. 9—Measurements, the following reference numerals:

30. Drawing of placement of rack and stack of video conferencing equipment
31. Firewall position 32. Example of materials used in actual Prototype Two. Drawing indicates external laminate with interior of aluminum. Foam core is installed between laminate and aluminum for greater density and improvement of audio and sound For FIG. 10—View of possible floor plan with multiple stations in larger Prototype Three design of invention, the following reference numerals:

33. Shows multiple video conferencing stations floor plan inside shelter.

For FIG. 11—Curbside view of Prototype Three version of the invention, the following reference numerals:

34. Video conferencing equipment view
35. Storage, electrical supply and connections box For FIG. 12—Exterior Curbside view of training and teaching hospital application drawing of Prototype Three of invention, the following reference numerals:

36. Shows flatbed design of unit on wheels for easy transporting
37. Computer and video conferencing training section of unit
38. Telemedicine (medicine conducted through video conferencing over a distance via communications links such as satellite or terrestrial transmission) hospital and medical and training section with video conferencing equipment, operating table, space for sterile medical storage, and medical peripherals
39. Medical entrance door in preferred embodiment, the shorter doors will have a platform and hydraulic lift to better access patients in wheelchairs or on stretchers and gurneys
40. Satellite dish connected to Prototype Three shelter to receive and transmit two-way video conferencing signals.

The invention is an enclosed, secure shelter that houses people as shown in FIG. 8, and houses equipment 23 also shown in FIG. 8, for the sole purpose of conducting two-way interactive video conferences. The video conferences conducted can be point-to-point, from one location to another location, or multipoint conferences where many locations meet together in one video conference.

This invention has alternative shelter embodiments, yet all the embodiments have doors 1 and 18 as shown in FIGS. 1 and 7, windows 2 and 8 as shown in FIGS. 1 and 3, walls 32 and 33 as shown in FIGS. 9 and 10, floors, roof 10 and 14 as shown in FIGS. 4 and 5, vents 14 and 19 and 29 as shown in FIGS. 5, 7 and 8, firewalls 9 and 28 and 31 as shown in FIGS. 3, 8 and 9, video conferencing lighting 27 as shown in FIG. 8, equipment and door locks 4 as shown in FIG. 1, equipment racks 7 and 16 and 23 and 30 as shown in FIGS. 3, 6, 8, and 9, pullout writing panels 24 as shown in FIG. 8, lighted in-use sign 3 and 5 according to FIGS. 1 and 2, equipment console 9 and 24 as shown in FIGS. 3 and 8, user identification devices, locked storage and equipment cabinets 4 as shown in FIG. 1, external and internal communication links, security measures, video conferencing specific acoustics and video enhancing materials, seating accommodations, and spaces for housing people and electronic equipment.

The invention is entirely enclosed as shown in FIGS. 1, 8 and 12. One embodiment of the freestanding booth/kiosk shelter enclosure prototype has a layout according to FIG. 9. Custom graphics can be added to the shelter upon request, such as logos and pin stripes. A variety of color-schemes are available for the laminate, or other selected building materials, and also for the borders. The current embodiments of the booth/kiosk shelter are linear as shown in FIGS. 1, 7, 8, and 10. The cosmetic design of the booth is subject to needs and desires of applications and clients. The main compartment in a preferred embodiment is made from high-density foam 32 as shown in FIG. 9, and covered with a high impact mar resistant laminate. Both the interior and exterior materials can be customized to client's requirements, such as aluminum or steel, or weather resistant and spill-proof materials. Interior and exterior colors (including any logos or racing stripes) and materials will be determined by customer at time of purchase. Other alternative materials can be utilized in other embodiments.

A preferred embodiment of this invention has a floor of a claded panel of plywood, which is carpeted or treated with a non-skid material. The roof is a bonded panel, which includes air vents 29 as shown in FIG. 8, ducting and connections for the cooling systems. The weight of preferred embodiment of the booth/kiosk shelter, less the installed seat bench 6 and 11 and 25, as shown in FIGS. 2, 5 and 8, and the equipment is approximately 400 lbs. Alternative materials are possible and the weight will vary in embodiments of the shelter.

A firewall is in place between the user compartment 28 as shown in FIG. 8, and equipment cabinet. The equipment cabinet where all equipment is stored is behind a locked door 4 as shown in FIG. 1, this locked door acts as a deterrent for theft, and for easy, secure access for equipment troubleshooting.

The lighting 27 as shown in FIG. 8, is very important in video conferencing. In this invention, particular attention is made to the lighting source; lights typically produce between 65-80 foot candles in the vertical plane. Windows are of many shapes, and a preferred example of windows are the V-shaped 20 as shown in FIG. 8 version in prototype two. The windows in these enclosed shelters can be see-through glass, one-way mirrors, smoked or other types and materials of glass.

The preferred embodiment for seating in this invention is a comfortable fold-down seat, or an alternative moveable chair or chairs as part of the shelter structure. Alternative seating can be utilized. One preferred embodiment of the invention has a pullout writing desk, with an electronic graphics art pad imbedded in the pull out shelf for automatic remote writing and electronic signature generation.

In another preferred embodiment, as seen in the second prototype FIGS. 7, 8, and 9 of this invention, the main compartment is symmetrical, approximately four feet by four feet, by seven and a half feet tall. The main compartment is made from high-density foam 32 as shown in FIG. 9, covered with a high impact mar resistant laminate. The wall thickness of the second prototype is ⅝ inch thick. The first prototype built of this invention had other measurements and materials as seen in FIGS. 1 and 3.

Since the United States Government has mandated the elimination of CFCs (chloroflourocarbons) and halons. In order to comply with the Montreal Protocol on substances that Deplete the Ozone layer, the shelters use ISOFOAM, SS-1339 (spray foam) in lieu of CPR 832-2 and CPR485D, ISOFOAM, SS-1339 foam meets the requisite physical properties required for shelter spray foam applications.

Acoustical 32 as described in FIG. 9 specifications are as important as video reception within a video conferencing shelter or enclosure. The interior portion of the preferred embodiment of the shelter has a minimum of −30 dB SPL, with a weight isolation from the environment surrounding the booth/kiosk shelter. The interior portion of the shelter has a minimum of −20 dB SPL, A weight, isolation from the equipment area of the booth/kiosk shelter. The equipment area of the booth/kiosk shelter has a minimum of −20 dB SPL, A weight, isolation from the environment surrounding the shelter. The interior portion of the shelter has a reverberation time of between 0.4 and 0.8 seconds. The combined noise caused by fans, etc., in the equipment area of the booth/kiosk shelter does not exceed 65 dB SPL, C weight.

Entry to the shelters is done in the preferred embodiment by inserting a card, such as a smart card 17 as depicted in FIG. 7, or creditcard into a magnetic swipe cardreader 3 as shown in FIG. 1. This cardreader can connect to a modem, or to another system, or to an EDI (Electronic Data Imaging) services, or to a custom interface designed with the card reader. A custom set-up of the cardreader can be designed to use with most credit cards, or custom-designed software to only allow accessibility to participants holding an issued debit card.

The use of a custom software interface to the cardreader, can include data collection software, and billing and automatic letter generation can be set up to be a part of the software system.

With the preferred embodiment with a smart card scanning device, other security methods, measures and devices, such as voice, pattern, retina recognition devices, magnetic swipes, or fingerprint readers can allow for greater security presence permitting access to only those participants with the proper identification. This feature serves as an accountability and safety measure to the insure that the use of the two-way enclosed video conferencing shelter is not tampered with unless entered into with proper identification. The smart card access also deters theft of the enclosed equipment. In a preferred embodiment the card reader is installed on the shelter next to the in-use lighted sign 3 and 5 as shown in FIGS. 1 and 2.

The shelters are equipped to provide full telecollaboration and electronic one on one, or face-to-face, or point to point conferences, as well as multipoint video conferences by connecting to one or to many video conferencing locations and systems. In the preferred embodiment the shelters connect interactively in two-way video conferencing meetings over any and all types of communication transmission media. These shelters are fully integrated and configured for interoperability and compatibility with other video conferencing systems and communication carriers. This invention of enclosed two-way interactive video conferencing shelters stores and houses all configurations and all electronic installations necessary for the complete operation of an interactive two-way video conferencing meeting in the frame of the shelter.

In the preferred embodiment of the enclosed shelter equipment is carefully integrated and interfaced 22 as shown in FIG. 8 to existing networks.

Black boxes, or network termination equipment interfaces the image and information acquisition equipment with the outside (interfacility) network. The network termination equipment accepts the information sent to it by image and information acquisition equipment and coverts it to an electronic format that can be transmitted over the interfacility network. These enclosed, secure, two-way interactive video conferencing shelters can be designed to interface and connect to various transmission media, including but not limited to digital copper, coaxial cable, optical fiber, digital microwave, digital satellite, and dial-up services like ISDN (Integrated Services Digital Network) or Switched 56 Kbps service. Since two-way interactive compressed video is an intregal part of the shelter then multiplexed ISDN could be a switched service option. Other alternatives could be fractional T1 or dedicated full T1. If full motion 45 Mbps (megabits per second) video is preferred for some application, then probably ATM (Asynchronous Transfer Mode) technology would be applicable. Other communication media will be considered in future embodiments and design.

Regardless of the transmission media, the preferred embodiment of this invention interfaces with all electronic networks and transmission carriers, and provides necessary elements for connectivity to all internal and external video conferencing transmission carriers and sources. Various modes of transmission, including satellite connectivity is built into the shelter, for instance, a satellite dish 40 as shown in FIG. 12, can be connected to the shelter to receive and transmit two-way interactive video conferencing signals and content. intra facility networking interfaces and network termination equipment.

In the preferred embodiment of the invention it offers, but is not limited to the following equipment: A video conferencing camera 15 and 27 as shown in FIGS. 5 and 8, and codec running from 15 frames to 30 frames per second. Either can be integrated into the unit; a computer and a color computer video monitor; a VCR where users can record or play video; a control pad screen with already programmed menus designed for two types of users. A non-computer user has a simple push-button menu (push to make a call, enter a number, volume up and down, view camera, view the VCR, and so forth ) with instructions on the touch screen positioned on the console 9 as shown in FIG. 3. And, a second kind of user, a computer literate user, has an impressive menu of choices for effortless telecollaborative sharing. In the preferred embodiment, a telephone is embedded in the console, or attached to the inside wall 9 and 26 as shown in FIGS. 3 and 8. Various equipment can be used in alternative embodiments of the two-way interactive video conferencing and telecollaborative interactive shelters. These moveable, or transportable enclosed shelters are subject to various electronic equipment and technologies to allow for customized applications.

Two-way video conferencing interactive meetings are accomplished through the use of various compressed or full-motion interactive video systems and equipment, including, but not limited to virtual reality equipment, electronic equipment and peripherals, image information equipment, video conferencing equipment, cameras, and codecs, telephones, central processing units and computer hardware and software, color computer and video monitors 12 and 23 as shown in FIGS. 5 and 8, video cassette recorders 13 as shown in FIG. 5, control touch pads with programmed software menus, graphic art pads, speakers and audio equipment, electronic switches, audio-graphics systems, fax machines, document scanning devices, a control panel or box, printers, and, application specific electronic imaging and video conferencing devices. Any or all of the above listed equipment 23 and 30 as shown in FIGS. 8 and 9, can be a part of the invention. In the preferred embodiment this equipment is placed and operated from inside the enclosed shelter. The equipment compartment in the shown smaller shelters is three feet by four feet in size 4 and 7 and 16 and 21 as shown in FIGS. 1, 3, 6, and 8. This compartment houses all electronic equipment and a power distribution center.

The electronic equipment, hardware and software in the preferred embodiment is positioned and tied into a rack and stacked within the equipment chimney 30 as shown in FIG. 9. This rack and stacking approach allows for easy troubleshooting and integration of the equipment. In the preferred embodiment, each shelter has all the electronic system integration needed for full operation of the video conferencing shelter, and all the electronic components needed to conduct effective two-way interactive video teleconferencing either point-to-point or multipoint. The equipment fits on a rack measuring is approximately 22"×22"×4 feet. The weight of the electronic equipment in the booth/kiosk embodiment of Prototype Two as shown in FIG. 8 is approximately 150–200 pounds.

Alternate shelter embodiments can utilize this invention, for example, a severe-weather proofed shelter can mount directly on the roof a small digital satellite receiver 40 as shown in FIG. 12, for remote reception, while placed and functioning with two-way interactive video conferencing from a freezing part of the globe. Different layouts of the enclosed two-way video conferencing interactive shelter might provide multiple seating stations 34 as shown in FIG. 11 that can house small groups of people.

Another alternative embodiment provides an operating or extra video conferencing room 38 as shown in FIG. 12, for an examiner and a patient. Another possible application and embodiment of the larger shelter unit is for a training and teaching hospital 37 as shown in FIG. 12, with a flatbed design, tractor-trailer wheels for easy transporting, a computer and video conferencing workstation training section where telemedicine (medicine conducted through two-way interactive video conferencing over a distance via communications links such as satellite or terrestrial transmission) or training is conducted through video conferencing equipment offers wheelchair accessibility. A telemedicine operating room setup 38 as shown in FIG. 12, with sterile medical storage spaces, various medical peripherals, has an entrance door with a platform and hydraulic lift to better access patients in wheelchairs or on stretchers and Gurney. This embodiment of the invention is wheelchair accessible, and access to the shelter is through a wheelchair accessible door 1 and 39 as shown in FIGS. 1 and 12. All the enclosed two-way interactive video conferencing embodiments of the shelter provide for wheelchair accessibility.

A shelter can have spaces that allow for several projects to take place concurrently; such as technicians or engineers working in the field in a remote area on technical products from within one larger transportable enclosure shelter as shown in FIG. 10, and connecting with a subject matter expert in a booth/kiosk shelter as illustrated in FIG. 9, enclosure located in a public building in a urban city.

It is also possible to provide other elements to this invention, for instance in order to place the booth/kiosk shelter in an external location given to temperature extremes, the insulation and weather-proofing material of the booth/kiosk shelter needs to be selected to accommodate such weather.

Another preferred enclosed example drawing of this transportable or moveable shelter is Prototype Three as shown in FIGS. 10 and 11, which has multiple two-way interactive video conferencing workstations, equipment and electrical storage 35 as shown in FIG. 11, compartments, and electrical supply and connections box. This shelter embodiment, when used in a medical application has a separate telemedicine operating room 38 as shown in FIG. 12. This larger interactive two-way video conferencing shelter is equipped to provide teleradiology and still images, teledermatology, telecardiology, telepsychiatry, teledermatology, or telesurgery. Medical peripheral equipment and devices are used in these larger on-the-road shelters, such as blood pressure monitors, dental exam camera, dermatology cameras (dermatoscopes), electrocardiography systems (ECGs), electroencephalograph systems (EEGs), fundocopes, IV infusion pumps, ophthalmoscopes, and otoscopes. Other preferred equipment to be installed and used in a larger enclosed two-way video conferencing shelter for a telemedicine application will include patient exam cameras, pulse oximeters, videoendocscopes (gastroscope, bronchoscope, etc.), videomicroscopes and other selected medical equipment.

Less than 100 years ago man had no electricity and our bodies lived in harmony with the natural frequency of the earth. This resonance has been recently measured at 7.83 Hz and is call the Schumann resonance. When this signal is altered for a period of time, reproductive and other systems of the body are directly affected. If you measure the natural frequency emission of the human brain, the brain's signal is identical to the frequency emitted by the earth. The electrical activity of the earth is like a giant brain.

Electromagnetic waves will penetrate at the cellular level and enhance the immune system, heal fractures, as well as other noninvasive methods of healing from either a single peripheral inside the unit to shielded walls of electromagnetic waves that comprise panels inside the four walls of the units. There are other medical or alternative healing devices and entire wall units of peripherals that will be used as well in healing.

Certain specific locations on the anatomy where the electrical flow is much more conductive, and these points generally correspond to the Eastern Medical Acupuncture points. One can use an impedance or OHM metering to test the acupuncture points leading to the measurement of the flow to be offered from the devices on this invention. This invention will measure the electrical impedance through Electro-Acupuncture Testing, vibrational physiology through measurement of sound vibrations.

The use of a screening watch that measures organ energy levels could be issued for users of these booth/kiosks. The patient could drop the watch into a scanning or reading device to determine the values and dysfunctions in their ambient electromagnetic fields. This watch could have a dual purpose of measurement, as well as shield human cells from electromagnetic fields and allow the cells in the human body to increase its immune production, and decrease its uptake of depression inducing chemicals. There are already such watches on the market. This invention would be a data collection repository for statistical data and provide service for the devices.

The following formulation of concepts regarding physiology appears to have utility, and instruments which take measurements based on these concepts have data outputs which can be remotely and securely monitored using the present invention. Vibrational medicine, which is based upon the Einsteinian concept of matter as energy, and of human beings as a series of complex energy fields in dynamic equilibrium. Different parameters of measurement, from time distortion to alteration of length, width, and mass, may vary according to the velocity of the system being described. For instance, negative space/time is the dimension of the etheric world of energies, which includes the human etheric body. The substance, which makes up our etheric bodies, vibrates at speeds faster than light, making it difficult to directly measure with conventional electromagnetic sensing equipment.

Sensors

There is considerable evidence to suggest that there exists a holographic energy template associated with the physical body. This etheric body is a body, which looks quite similar to the physical body over which it is superimposed. It is believed that within the etheric energetic map is carried information, which guides the cellular growth of the physical structure of the body. It the structural data for growth and repair of the adult organism should damage or disease occurs.

The physical body is energetically connected and dependent upon the etheric body for cellular guidance. If the etheric field becomes distorted, physical disease soon follows. Many illnesses begin first in the etheric body and are then later manifested in the physical body as organ pathology. The etheric body is, in fact, a body of matter. The matter of which it is compose is called "etheric matter" or "subtle matter." It is the substance of which our higher energetic bodies are composed. Subtle matter is used as a general term referring to types of matter associated with our unseen, higher energetic counterparts. The only difference between the etheric body and those higher bodies is that of frequency characteristics. The higher energy bodies are unseen only because the technologies, which render these energies visible to the naked eye, are still mostly in the developmental states.

Meridian

It would appear that the meridian system (which provides a type of intermediate road map used in acupuncture) forms an interface between the etheric and the physical body. The meridian system is the first physical link established between the etheric body and the developing physical body. The meridian system is not just a physical system of tubules transporting hormones and nucleotides to cell nuclei, but is also a specialized type of electrolytic fluid system that conducts certain types of subtle energies (ch'i) from the external environment to deeper organ structures.

The implication that certain types of energies are communicated through the acupuncture points of the superficial meridian system is supported by measurements of electrical skin resistance in and around the acupoints. Quantitative measurements by various researchers have demonstrated that there occurs a nearly twenty-fold drop in electrical resistance at the acupoints. It is well know that energy tends to follow the pathway of least resistance Charkas Data seems to confirm the existence of the charka system. The energies measured coming from the charkas in each of the experiments were composed of lower harmonics of the original higher frequency subtle energies. All these energies are merely octaves of the electromagnetic spectrum. The primary energy centers on the human body are called charkas. These are the non-physical organs of the energy body. There are at least seven primary centers, and over three hundred secondary and minor centers, scattered throughout the human body. All together, they form a complex network of non-physical energy components. These are all joined together by interconnecting pathways, or meridians.

These centers, and their interconnecting pathways (meridians) were charted by the Chinese, and other Eastern races, thousands of years ago. Modern versions of these charts are still widely used today, in many types of alternative medicine and bodywork, i.e., acupuncture and reflexology.

Primary energy centers are attached to major internal organs, glands, nerve ganglia and the spinal cord. Secondary and minor energy centers are attached to joints, glands and nerve clusters, throughout the body. There are active centers transforming and manipulating energy feeding other energy centers and taking care of life processes, both physical and non-physical.

Energy centers are invisible to the naked eye but can be felt, quite strongly, when they are active (as a pulsing, thrumming sensation). When energy is consciously drawn from one center to another, through the connecting meridians, this can be felt as: A rushing water sensation, a spreading warmth, a tingling feeling, or a combination of these.

Energy centers (charkas) can also be seen-with auric and clairvoyant sight, as whirling vortexes of intensely colored light. The energy field of the body itself will be measured, as well as the human aura that is an energy field that surrounds the human body, and reflects the subtle life energies at work within and around it. This is something like the magnetic field that surrounds a simple magnet. Like a magnetic field, the aura is generated within physical matter ùbut is also affected by its surroundings. The energies flowing through the aura make us what we are, and are in turn affected by our surrounding life conditions and life style. The aura reflects the activity of our organs, health, mental activity and emotional state.

The aura also shows disease, often long before the onset of physical symptoms. Our subtle energetic components, i.e. the charkas and the meridian system, translate our emotional and spiritual difficulties into physiological weaknesses, which may eventually result in a localized system breakdown in the physical body, i.e. disease. When disease occurs, it is a symbolic warning message that something has gone wrong in the system. The area of constriction needs to be rebalanced if lasting health is to be achieved.

Other peripherals in this invention will be used to measure the aura (the energy field surrounding the human body) can be attached to the video conferencing camera in this invention or to an imaging device that can pick up the acupuncture, reflexology and charka points from the individuals' hand placed on the imaging scanner. This concept is easier to understand when considering that all things in the universe including humans, vibrate at certain levels.

Every energy center has important individual functions, in the energy body. It also works in conjunction with all the other major and minor centers. Each center is an individual, but integral part of the energy body. They all work together, for the good of the whole energy body; just al all the physical organs, brain, heart, liver, kidneys, glands, and so forth, work together for the good of the whole physical body.

The energy body is similar to an electronic device. Energy flows into the electronic device, and on through connecting pathways (meridians) that are etched into the circuit board. These connecting pathways (meridians) carry energy on to all it's electronic components (charkas), diods, resistor, capacitors, etc. energy is continually being changes, enhanced and transformed, by these components; to serve a multitude of different purposes, required by the device, as a whole unit, to function properly.

A single energy center, is very much like a single electronic component. It takes in energy from the components around it, and changes the value of it. It enhances this energy, in various ways, transforming it into something different, that is needed by the whole unit.

Each energy center (charka) takes in the different types of energy it requires, from other energy centers in the energy body, and generates a completely different type of energy, with a different value and color according to what is required. Energy healing and the use of auric sight as an aid to diagnosing or assessing the health of patients will be a principal use of this invention.

The etheric body is, in fact, a body of matter. The matter of which it is compose is called "etheric matter" or "subtle matter." It is the substance of which our higher energetic bodies are composed. Subtle matter is used as a general term referring to types of matter associated with our unseen, higher energetic counterparts. The only difference between the etheric body and those higher bodies is that of frequency characteristics. The higher energy bodies are unseen only because the technologies, which render these energies visible to the naked eye, are still mostly in the developmental states. The world of radio and x-ray astronomy was also an unseen universe until the appropriate technologies could be developed to extend our senses in those energetic directions. So, in the case of subtle energies, a similar research effort in rendering the invisible visible is greatly needed at this time.

What is important is that there are various intricate systems, such as the meridian and charka-nadi networks, which integrate the etheric body with the physical body. Technology has now moved to the point where validation of these previously described subtle energetic links with our physical anatomy may be confirmed and elaborated upon. This invention will focus on the measurement, assessments, and healthcare of the etheric body.

A more complete understanding of how the etheric body interrelates with and affects disease expression in the physical body will provide valuable information to a new breed of physicians who are attempting to evolve beyond traditional medical dogma in their attempts to create new and more effective approaches toward healing human illness.

The meridian system is not, however, the only link between our physical body and our higher energetic systems of functioning. The charkas centers of the body could indeed activate and direct energy, and the bioenergetic or bioelectrical output from these centers could be measured.

Even thought the primary energy conducted though the charkas might be of a subtle energetic nature, secondary reverberations of energies in a lower octave harmonic, such as electrostatic fields, might be measurable. The electrostatic fields are only secondary effects produced by the higher octave etheric energies, but they are more easily measurable with conventional electronic recording equipment.

There have been studies combining conventional measuring equipment of the charkas and the human energy field such as EMG electrodes to study bioelectrical energy variations in areas of skin corresponding to the positions of the charkas. Accompanying the electrical measurements, trained psychic observers, who could clairvoyantly see the changes occurring within an individual's auric field while the charkas were being electronically monitored. It was found that the physic auric observation, relating to color changes in the subject's energetic field, correlated exactly with the EMG electrode recordings. From within this invention, trained physic observers, physicians, clinicians and healers will measure, research, and study the changes in an auric field with energetic medical peripherals.

Each color of the aura is associated with a different wave pattern recorded at the charka points on the skin of the subjects. The wave patterns became named after the auric colors with which they were found to be associated. There are devices that measure colors and wave patterns in the assessment of the health of a person.

Another vibrational remedy is color tinctures. Video conferencing is ideal for this treatment. Color treatment, color therapy, or chromotherapy has many forms and applications. Many esoteric color theorists feel that the colors of light in the visible spectrum are lower octaves of higher vibrational energies that contribute to the auric field and subtle bodies.

Esoteric sources refer to these higher octaves as the seven major rays, which influence the personality nature and growth of the soul. These seven rays are of celestial origin. Their characteristics are beyond the scope of this patent information, but specific references provided in the follow chart will act as a guide:

Chart of Subtle Energetic Effects of Color

| COLOR | Charka | ENERGIES | DISEASE AFFECTED |
| --- | --- | --- | --- |
| VIOLET | Crown Charka | Higher Mind | Nervous & Mental Disorders |
| INDIGO | Third-Eye Charka | Vision | Disorders of the Eye |
| BLUE | Throat Charka | self-expression | Thyroid & Laryngeal Diseases |
| GREEN | Heart Charka | Inner Harmony | Heart Disease & Hypertension |
| YELLOW | Solar Plexus Charka | Assimilation Circulation | Disorders of Lungs & Kidneys |
| ORANGE | Spleen Charka | Assimilation Circulation | Disorders of Lungs & Kidneys |
| RED | Root Charka | Vitality Creativity | Blood Disorders Anemias |

Each major visible color has particular qualities that are linked to the charka with which it resonates. An understanding of the nature of the charkas and their higher energetic links to body physiology helps one to understand the reasons for using particular colors to heal specific illnesses.

Each color of the aura is associated with a different wave pattern recorded at the charka points on the skin of the subjects. The wave patterns became named after the auric colors with which they were found to be associated. When colors such as "white light" were seen in the auric field, the frequency signal measured was over 1000 cps. It was hypothesized that this high frequency level is actually a subharmonic of an original frequency signal which is in the range of many thousands of cycles per second: a subharmonic of the original charka's subtle energy. Various vibrational modalities will be in use in the Alternative Medical Model of this invention.

It is the intent of this invention to use measurement devices to measure these subtle energies. As the new technologies evolve, and imaging systems are developed which can better capture the subtle energies and multidimensional fields of the human anatomy, vibration medicine will become more widely accepted by those within the more orthodox medical establishment. This invention will house measurement devices and peripherals to measure and assess these subtle energies.

Laser systems, electronic sensors or optics (i.e. light detection and ranging) are other devices for the purposes of health assessment and diagnostic peripherals in this invention. Laser surgery currently is providing non-lethal lasers that are meant to generate very bright omni-directional light, with similar effects to laser guns. The capability is within medical science's grasp to use Infrared and laser technologies to measure meridians and energy fields on the human body. It is the intent of this invention to use infrared devices for the purposes of health assessments and diagnostics.

Infrared therapy has proven to be particularly effective in the healing treatment of pain and inflammation. Powerful infrared therapy combined with additional frequencies (colors such as visual red has produced very rapid, sustained results). If a device installed in this invention of a proper frequency could trigger a healing effect then the damaged area exposed to such as device would lower the gate threshold of local nerves and fire them allowing the body to bring in endogenous chemicals needed to heal. Infrared devices or peripherals allow for the natural nerve and cellular stimulation virtually without side effects or increased trauma to the treated area.

The therapeutic applications of low energy photons if delivered at specific powers, frequencies and wavelengths can interact with body tissues and can relieve a number of painful conditions. The photons must be specifically defined for the condition being treated. And must be calibrated with wavelength, monochromaticity, beam divergency, pulse frequency, pulse duration, power intensity, does, and three-dimensional light distribution in the tissue. Each condition being treated requires unique stetting. Certain wavelengths have been found that will penetrate the skin to different depths. A low energy photon focusing on acupuncture, tender, or trigger points may be used with light emitting or laser diodes to facilitate a treatment or assessment inside this invention following clinical protocols.

Infrasound-acoustic beams utilizing methods of projecting non-diffracting (i.e. nonpenetrating) high frequency acoustic lasers will be a preferred method to record data from acupuncture points and measure skin resistance leading to health assessments. Devices or peripherals or methods of using pulsed chemical lasers that could project a hot, high pressure plasma in the air in front of a target surface, creating a blast wave that will result in variable but controlled effects on material and personnel may evolve to be a preferred device for health assessments inside this invention.

Very Low Frequency (VLF) sound (20–35 KHz), or low frequency RF modulations can cause the disruption of human organs and could lead to medical breakthroughs in reversing diseases. The use of VLF in this invention may be coupled bouncing radio or microwave signals to affect physical or mental functions of people to promote healing.

The history of Auras begins as far back as the first person that saw a glow around other people. Today, modern researchers measure the aura as an electromagnetic field, which surrounds all living creatures. Kirlian photographic studies have confirmed that acupuncture points have distinct electrographic characteristics. Utilizing abdominal electron graphic body scans this invention will assess and record the changes in brightness of the acupuncture points that precede the changes of physical illness in the body by hours, days, and even weeks.

Kirlian electrography and various other acupuncture-related electronic systems may have great diagnostic potential for future physicians. Such devices can measure subtle physiological imbalances in the body associated with illness earlier than existing methods.

This invention will provide biofeedback photography. Aura Photography is a process that measures the Electro Magnetic Field around the body, attached to the camera is a hand plate that can pick up the acupuncture, reflexology and charka points from the individuals' hand and relay that energy information to the camera. It would appear that the meridian system (provides a type of intermediate road map used in acupuncture) forms an interface between the etheric and the physical body. The meridian system is the first physical link established between the etheric body and the developing physical body. The meridian system I not just a physical system of tubules transporting hormones and nucleotides to cell nuclei, but is also a specialized type of electrolytic fluid system that conducts certain types of subtle energies (ch'i) from the external environment to deeper organ structures.

The implication that certain types of energies are communicated through the acupuncture points of the superficial meridian system is supported by measurements of electrical skin resistance in and around the acupoints. Quantitative measurements by various researchers have demonstrated that there occurs a nearly twenty-fold drop in electrical resistance at the acupoints. It is well know that energy tends to follow the pathway of least resistance.

The meridian system is not, however, the only link between our physical body and our higher energetic systems of functioning. The charkas centers of the body could indeed activate and direct energy, and the bioenergetic/bioelectrical output from these centers could be measured. Even thought the primary energy conducted though the charkas might be of a subtle energetic nature, secondary reverberations of energies in a lower octave harmonic, such as electrostatic fields, might be measurable. A similar line of reasoning has been used to help explain how lower octave electrons in Kirlian photography can be used to visually capture higher dimensional etheric phenomena such as the Phantom Leaf Effect. The electrostatic fields are only secondary effects produced by the higher octave etheric energies, but they are more easily measurable with conventional electronic recording equipment.

There have been studies combining conventional measuring equipment of the charkas and the human energy field such as EMG electrodes to study bioelectrical energy variations in areas of skin corresponding to the positions of the charkas. Accompanying the electrical measurements, trained psychic observers, who could clairvoyantly see the changes occurring within an individual's auric field while the charkas were being electronically monitored. It was found that the physic auric observation, relating to color changes in the subject's energetic field, correlated exactly with the EMG electrode recordings.

The newer systems of subtle-energy medicine not only relieve the symptoms of illness, as does traditional medicine, but they also address the emotional, mental, bioenergetic, subtle environmental, and spiritual causes of disease. This invention will scan energies, provide the means for face-to-face consultations, health assessments and diagnostics, and collect data through the EDI for a research base to add to the data on the new field of emerging medicine, and the needed clinical testing and information to grow the field. This invention with its medical scanning and measurement devices, two-way interactive video conferencing, audio, and billing and entry components is the instrument the energetic healing field has been seeking.

Vibrational medicine appears to hold some of the answers for a world that seems quite ill, but it will only work if there are inventions like this to access all humanity via electronics, data-warehousing and mining, transmission media such as the Internet, satellite and wireless technologies stretching into every hamlet and town on earth. In future embodiments a preferred medical peripheral device will be one that addresses the need to remotely touch the patient and would be part of the installed base of equipment. There are electronic gloves that work remotely today. They are touch sensitized, albeit in the development stages, but are the beginnings of touch over a distance. These peripherals and others will be possible choices and preferred equipment in the medical units of this invention.

This invention of an enclosed two-way interactive video conferencing shelter, regardless of size or embodiments, is mobile and transportable and can travel from place to place over land, sea, and air. The shelter is modular, can be setup and broken down into separate parts and moved from one location to another. A preferred embodiment of the shelter is modular, moveable, and transportable as illustrated in FIGS.

8 and 12. The preferred embodiment of the smaller booth/ kiosk shelter is modular, can be broken down and shipped in pieces and reassembled. This preferred embodiment has moveable walls that are replaceable if damaged, similar to replaceable parts on a build it yourself desk or other construct yourself or put together furniture parts.

All the alternative designs and embodiments of this invention are characterized as portable, or not stationary. Some of the larger transportable shelter embodiments actually have wheels 36 as shown in FIG. 12, allowing for transporting the entire shelter over land. Other preferred shelter embodiments are designed to lay on a flatbed as shown in FIG. 11, or a railroad car, and others are transportable in the air and water.

The preferable embodiments of this enclosed, secure, two-way interactive video conferencing shelters are that they are portable, moveable, mobile, as well as the modular. This invention can be used for conducting multipurpose video conferencing, such as, but not limited to applications like, two-way interactive real-time distance education and training, social services uses, medical uses, counseling uses, prison uses, legal uses, community development uses, and financial and business uses.

While the invention has been described in terms of preferred embodiments, those skilled in the art will recognize that the invention can be practiced with modification within the spirit and scope of the appended claims.

Having thus described my invention, what I claim as new and desire to secure by Letters Patent is as follows:

1. A modular enclosure for two way interactive video conferencing, comprising:

an enclosed structure, said structure further comprising an equipment compartment separated by a firewall from an adjacent user compartment;

a user door for secure access to said user compartment;

an equipment door for secure access to said equipment compartment;

accommodations for users in said user compartment;

video conferencing equipment removably mounted on a rack in said equipment compartment, said equipment having user interfaces, said user interfaces protruding through said firewall for availability to said users in said user compartment;

a console for user operation of said video conferencing equipment;

a telephone and a video camera mounted in said user compartment and connected to said video conferencing equipment through said firewall;

wherein said video conferencing equipment, console, telephone and video camera are usable by said users for two way interactive meetings, and wherein said enclosed structure, said user door, said equipment door and said video conferencing equipment conform to a modular design of said enclosure for ease of breakdown, movement to another location, reassembly and replacement.

2. A modular enclosure as in claim 1, wherein said user door provides wheelchair accessibility and said accommodations accommodate a wheelchair.

3. A modular enclosure as in claim 1, wherein said secure access to said user compartment is provided by a smart card usable to open said user door, said smart card being insertable into a smart card reader mounted in said user door, thereby providing an electronic record of said users, enabling easy access to billing, and acting to deter vandalism and theft.

4. A modular enclosure as in claim 1, wherein said secure access is provided by a voice recognition device.

5. A modular enclosure as in claim 1, wherein said video conferencing equipment includes blood pressure monitors, a dental exam camera, dermatoscopes, electrocardiography systems, electroencephalograph systems, fundoscopes, intravenous infusion pumps, ophthalmoscopes, otoscopes, pulse oximeters, gastroscopes, bronchoscopes or videomicroscopes.

6. A modular enclosure as in claim 1, wherein electronic network connectivity is provided to a plurality of video conferencing transmission carriers through a plug-in.

7. A modular enclosure as in claim 1, wherein said user compartment has foam core walls for improved sound having a minimum of −20 dB SPL within said user compartment, and wherein said equipment compartment has a plug-in to said equipment compartment for electronically connecting said video conferencing equipment to remote video conferencing systems.

8. A modular enclosure as in claim 7, further comprising a telemedicine application.

9. A modular enclosure as in claim 8, wherein said telemedicine application further comprises medical peripheral equipment.

* * * * *